United States Patent [19]

Moore

[11] Patent Number: Plant 6,679

[45] Date of Patent: Mar. 21, 1989

[54] BLACKBERRY—NAVAHO CULTIVAR

[75] Inventor: James N. Moore, Fayetteville, Ark.

[73] Assignee: University of Arkansas, Fayetteville, Ark.

[21] Appl. No.: 118,781

[22] Filed: Nov. 9, 1987

[51] Int. Cl.[4] ..... A01H 5/03

[52] U.S. Cl. ..... Plt./46

[58] Field of Search ..... Plt./46

*Primary Examiner*—Robert E. Bagwill

[57] ABSTRACT

Description and specifications of a new and distinct blackberry variety which originated from seed produced by a hand-pollinated cross of Arkansas Selection 583 (non-patented) and Arkansas Selection 631 (non-patented) is provided. This new blackberry variety can be distinguished by its thornless canes with erect growth habit, its late ripening, and its excellent fruit flavor.

2 Drawing Sheets

SUMMARY OF THE INVENTION

The new and distinct variety of blackberry originated from a hand-pollinated cross of Arkansas Selection 583 (non-patented)×Arkansas Selection 631 (non-patented) made in 1977 at the Arkansas Agricultural Experiment Station Fruit Substation at Clarksville, Ark. The seeds resulting from this controlled hybridization were germinated in a greenhouse in the spring of 1978 and planted in a field on the Arkansas Agricultural Experiment Station in Clarksville, Ark. The seedlings fruited during the summer of 1980 and one, designated Ark. 1172, was selected for its thornless canes, erect growth habit, and high fruit quality.

During 1981, the original plant selection was propagated asexually from root cuttings and a test row of 20 plants was established. Subsequently, larger test plantings have been established with asexually multipled plants at four additional locations in Arkansas and on state experiment stations in Illinois, Louisiana, Florida, Texas, North Carolina and Mississippi.

The new variety has been asexually multiplied annually since 1981 by the use of root cuttings and by rooting softwood cuttings. It forms new plants from adventitious buds on most root cuttings, but is best propagated by rooting softwood cuttings. During all asexual multiplication, the characteristics of the original plant have been maintained and no aberrant phenotypes have appeared.

Test plantings over a wide geographic area have shown this new variety to be adapted to differing soil and climatic conditions. It has performed well in tests in the Southeast U.S. but is not cold hardy in northern states.

Plants of the new variety are moderately vigorous and row establishment following planting is more rapid than with other thornless varieties. Both primocanes and floricanes are erect in growth habit and the new variety is the first truly erect thornless variety to be developed. The plants are genetically thornless, having the recessive genes for thornlessness derived from Merton Thornless. Plants and fruit are moderately tolerant to anthracnose (*Elsinoe veneta* (Burkh.) Jenkins), and plants are immune to orange rust (*Gymnoconia peckiana* (Howe) Trott).

Fruit of the new variety ripens late, about 15 days after the Cheyenne variety, and 7 days after the Shawneee variety, but about 5 days earlier than Dirksen Thornless, a standard thornless cultivar. Average ripening date is June 25 in central Arkansas. The harvest period is longer than most other erect varieties; it produces well for a full month. Fruit yields are comparable with the Cheyenne variety but are less than the Shawnee variety. Late spring budbreak avoids spring frosts and the new variety is consistent in yield from year to year.

The fruit is short conic in shape, bright glossy black in color and medium in size (ca. 5.1 g). The fruit is firm at maturity, consistently rating more firm than fruit of the Cheyenne and Shawnee varieties.

The fresh fruit has better flavor than any extant variety of thornless blackberry and is rated superior to the thorny varieties Cheyenne and Shawnee. The soluble solids content averages 11.2%, higher than most blackberry varieties. Seed size is smaller than other thornless varieties now in existence.

Fruit clusters are medium-large, cymose, and are borne on the periphery of the plant canopy, providing easy access to harvest. Flower fertility is high and clusters are well filled.

The new variety has been named the Navaho cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blackberry. Color terminology is in accordance with that of the Royal Horticultural Society Colour Chart published in 1966 by The Royal Horticultural Society of London, England.

Where dimensions, sizes, colors and other characteristics are given, it is to be understood that such characteristics are approximations of averages set forth as accurately as practicable.

The descriptions reported herein are from specimens group at Clarksville, Ark. unless otherwise noted.

Plant:

*Size.*—Medium, erect.

*Growth.*—Vigorous; prolific suckering from crowns, sparse suckering from roots.

*Productivity.*—High and for duration of one month; consistent from year to year.

*Cold hardiness.*—Medium, similar to Cheyenne.

*Canes.*—Erect, thornless. Cane diameter: Base 2.1 cm, midpoint 1.4 cm, terminal 0.3 cm. Internode length: Base 5.0 cm, midpoint 8.4 cm, terminal 3.4 cm. Floricane color: Base Brown Group (200B), midpoint Yellow-Green Group (152B), terminal Brown Group (200B). Primocane color: Base Greyed-Orange Group (175A), terminal Yellow-Green Group (146C) Date of primocane emergence April 2.

*Disease resistance.*—Moderate for anthracnose; immune to orange rust.

Foliage:

*Leaves.*—Large. Mature leaf diameter 7 cm; length 7.6 cm. Color: Floricane base Yellow-Green Group (147A), floricane terminal Yellow-Green Group (147B); Primocane base Yellow-Green Group (137A), primocane terminal Yellow-Green Group (137B).

Flowers:

*Date of first bloom.*—April 11.

*Date of last bloom.*—May 22.

*Blossom color.*—Yellow-White Group (158D) with occasional pink at border.

*Reproductive organs.*—Stamens — erect, numerous. Pistils — numerous. Pollen — normal and abundant.

*Number flowers per cluster.*—6.4.

*Number petals per flower.*—6.0.

Fruit:

*Maturity.*—Late, 15 days after Cheyenne. Average ripe date June 25, average period of maturity June 25–July 25.

*Size.*—Medium, average 5.1 g, uniform. Diameter primary fruit equator 2.3 cm, base pole 1.6 cm, terminal pole 1.2 cm; secondary fruit equator 2.0 cm, base pole 1.4 cm terminal pole 1.0 cm. Length: primary fruit 2.5 cm, secondary fruit 2.3 cm, tertiary fruit 2.2 cm.

*Shape.*—Short, conic, uniform.

*Color.*—Glossy black (Black Group 202A).

*Skin.*—Medium tender.

*Drupelet size.*—Medium (0.6 cm).

*Seed size.*—Medium large, 3.9 mg.

*Firmness.*—Good, superior to Cheyenne.

*Flavor.*—Very good, sweet.

*Soluble solids.*—11.2%.

*pH.*—3.01.

*Total acids.*—1.137%.

*Processed quality.*—Very good, superior to Cheyenne and Shawnee.

*Uses.*—Fresh and processed, jellies, jams.

The variety: The most distinctive features of the variety are its thornless canes with erect growth habit, late ripening, and outstanding fruit flavor.

I claim:

1. A new and distinct variety of blackberry, substantially as illustrated and described, characterized by its thornless, erect growing canes, late ripening, and excellent fruit flavor.

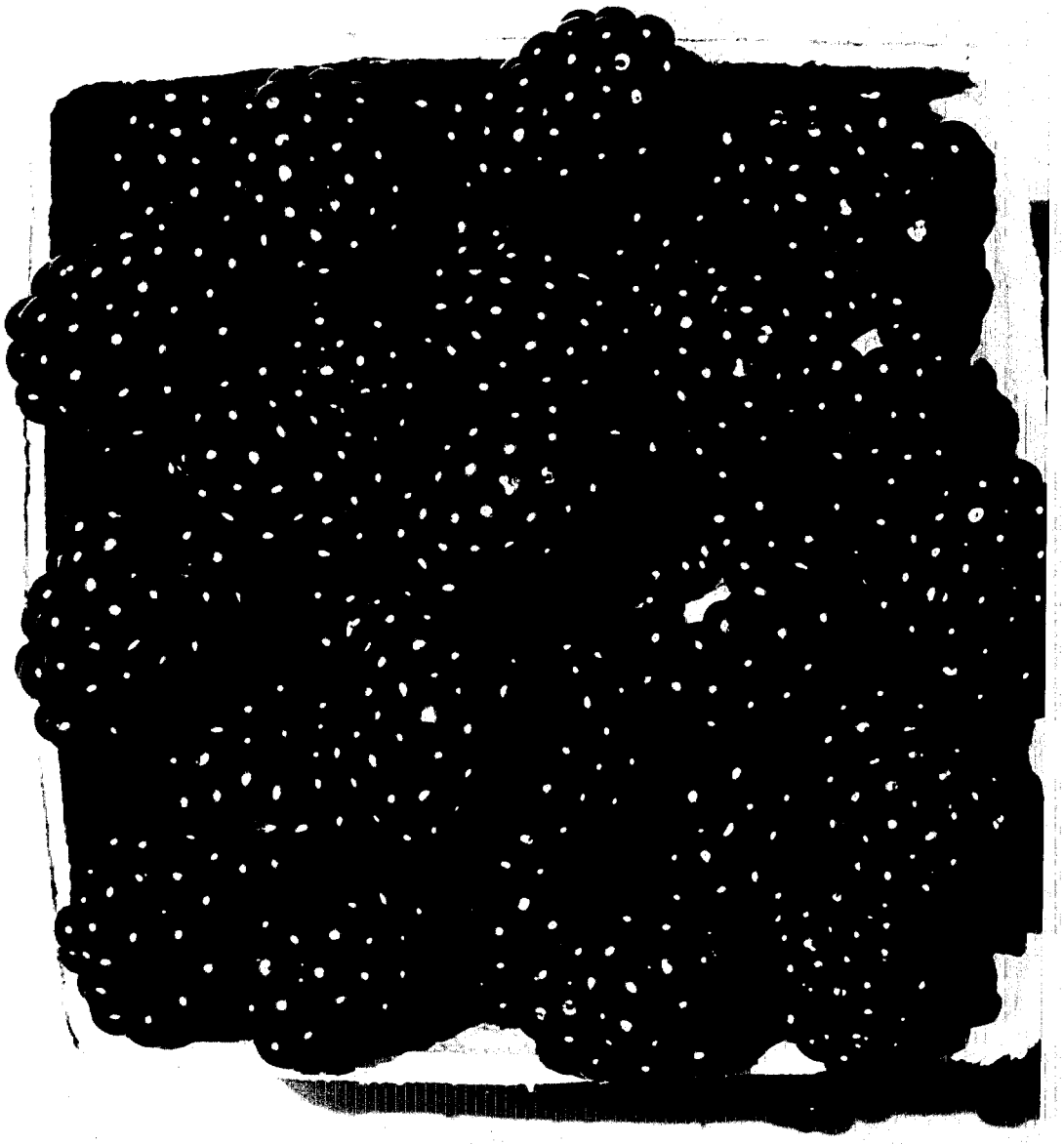

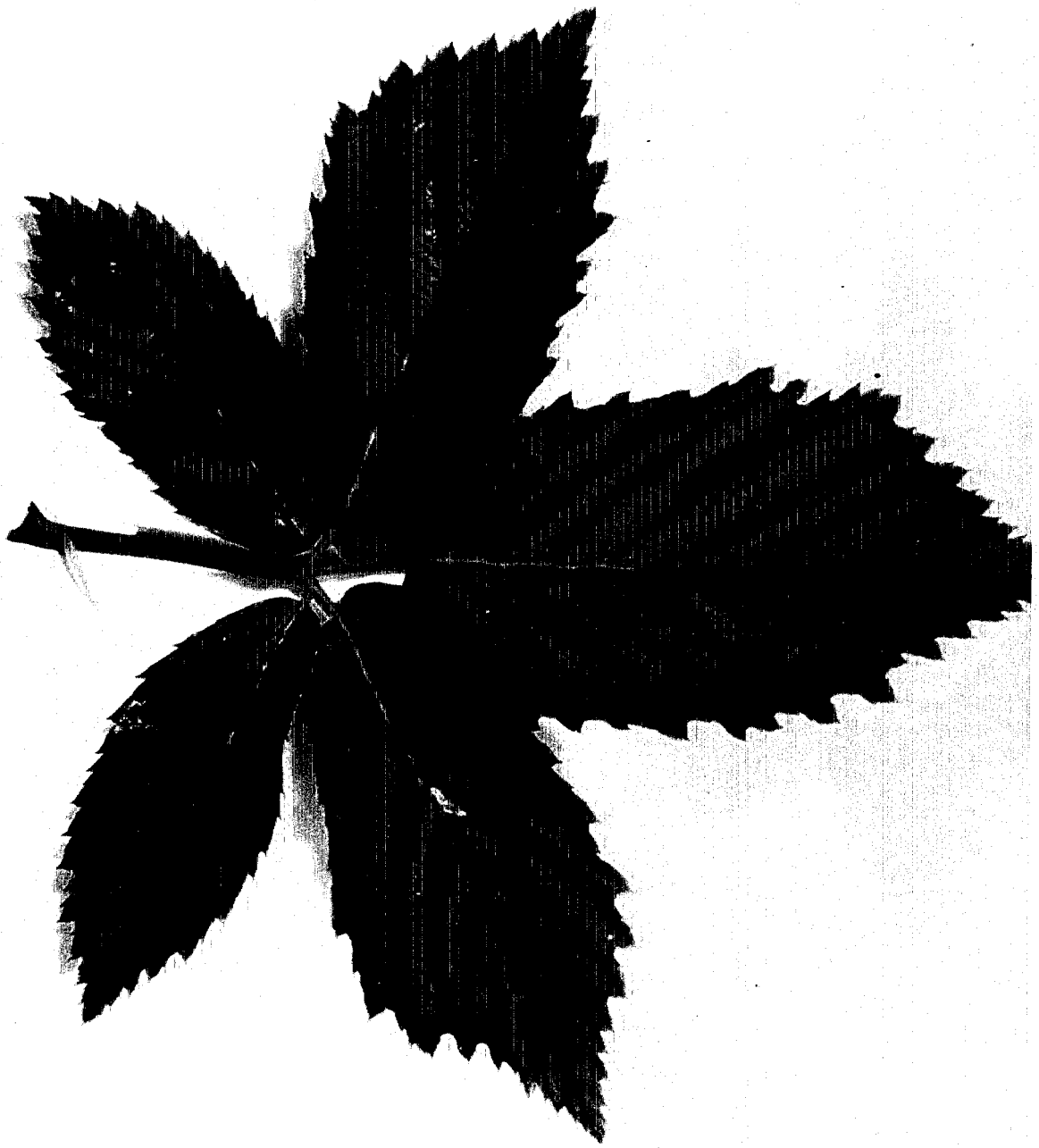

* * * * *